US009192912B1

(12) United States Patent
Mills et al.

(10) Patent No.: US 9,192,912 B1
(45) Date of Patent: Nov. 24, 2015

(54) CERAMIC NANOTUBE COMPOSITES WITH SUSTAINED DRUG RELEASE CAPABILITY FOR IMPLANTS, BONE REPAIR AND REGENERATION

(75) Inventors: David Mills, Monroe, LA (US); Yuri M. Lvov, Louisiana, LA (US)

(73) Assignee: Louisiana Tech University Research Foundation; a Division of Louisiana Tech University Foundation, Ruston, LA (US)

(*) Notice: Subject to any disclaimer, the term of this patent is extended or adjusted under 35 U.S.C. 154(b) by 0 days.

(21) Appl. No.: 13/446,775

(22) Filed: Apr. 13, 2012

Related U.S. Application Data

(60) Provisional application No. 61/475,016, filed on Apr. 13, 2011.

(51) Int. Cl.
 *B01J 20/16* (2006.01)
 *C08L 33/12* (2006.01)
 *A61C 5/08* (2006.01)

(52) U.S. Cl.
 CPC . *B01J 20/16* (2013.01); *A61C 5/08* (2013.01); *C08L 33/12* (2013.01)

(58) Field of Classification Search
 CPC ...... B01J 20/16; C08L 2666/58; C08L 33/12; A61C 5/08
 USPC .......................... 424/684, 422; 428/150, 41.5
 See application file for complete search history.

(56) References Cited

U.S. PATENT DOCUMENTS

| | | | |
|---|---|---|---|
| 4,059,684 A | 11/1977 | Gross et al. | |
| 4,098,676 A | 7/1978 | Robson | |
| 5,258,420 A | 11/1993 | Posey-Dowty et al. | |
| 5,492,696 A | 2/1996 | Price et al. | |
| 5,651,976 A | 7/1997 | Price et al. | |
| 5,705,191 A | 1/1998 | Price et al. | |
| 6,280,759 B1 | 8/2001 | Price et al. | |
| 6,401,816 B1 | 6/2002 | Price et al. | |
| 6,599,961 B1 | 7/2003 | Pienkowski et al. | |
| 6,713,527 B2 | 3/2004 | Bond et al. | |
| 6,872,403 B2 | 3/2005 | Pienkowski et al. | |
| 7,400,490 B2 | 7/2008 | Gunderman et al. | |
| 7,425,232 B2 | 9/2008 | Wang et al. | |
| 7,806,900 B2 | 10/2010 | Rabiner | |
| 7,811,290 B2 | 10/2010 | Rabiner | |
| 7,888,419 B2 | 2/2011 | Cooper et al. | |
| 2007/0106006 A1* | 5/2007 | Cooper et al. ................ | 524/445 |
| 2007/0202061 A1 | 8/2007 | Riedlinger et al. | |
| 2008/0200601 A1* | 8/2008 | Flores Santos et al. ....... | 524/445 |

FOREIGN PATENT DOCUMENTS

CN 1746216 C 3/2006

OTHER PUBLICATIONS

Frazer et al. PMMA: An Essential Material in Medicine and Dentistry. J Long-Term Effects Med Implants 15:629-639, 2005.*
Davis, J. M., and Hilary A. Cowie. "The relationship between fibrosis and cancer in experimental animals exposed to asbestos and other fibers." Environmental health perspectives 88 (1990): 305.
Donaldson, K., R. C. Brown, and G. M. Brown. "New perspectives on basic mechanisms in lung disease. 5. Respirable industrial fibres: mechanisms of pathogenicity." Thorax 48.4 (1993): 390-395.
Hart, Georgia A., and Thomas W. Hesterberg. "In vitro toxicity of respirable-size particles of diatomaceous earth and crystalline silica compared with asbestos and titanium dioxide." Journal of occupational and environmental medicine 40.1 (1998): 29-42.
Kommireddy, Dinesh S., et al. "Stem cell attachment to layer-by-layer assembled TiO2 nanoparticle thin films." Biomaterials 27.24 (2006): 4296-4303.
Lvov, Yuri M., et al. "Halloysite clay nanotubes for controlled release of protective agents," Acs Nano 2.5 (2008): 814-820.
Veerabadran, Nalinkanth G., et al. "Organized shells on clay nanotubes for controlled release of macromolecules." Macromolecular Rapid Communications 30.2 (2009): 99-103.
Abdullayev, Elshad, et al. "Halloysite tubes as nanocontainers for anticorrosion coating with benzotriazole." ACS Applied Materials & Interfaces 1.7 (2009): 1437-1443.
Vergaro, Viviana, et al. "Cytocompatibility and uptake of halloysite clay nanotubes." Biomacromolecules 11.3 (2010): 820-826.
Levis, S. R., and P. B. Deasy. "Characterisation of halloysite for use as a microtubular drug delivery system." International Journal of Pharmaceutics 243.1 (2002): 125-134.
Kelly, H. M., et al. "Formulation and preliminary in vivo dog studies of a novel drug delivery system for the treatment of periodontitis." International journal of pharmaceutics 274.1 (2004): 167-183.
Du, Mingliang, Baochun Guo, and Demin Jia. "Thermal stability and flame retardant effects of halloysite nanotubes on poly (propylene)." European Polymer Journal 42.6 (2006): 1362-1369.
Liu, Mingxian, et al. "Properties of halloysite nanotube—epoxy resin hybrids and the interfacial reactions in the systems." Nanotechnology 18.45 (2007): 455703.
Li, Cuiping, et al. "Polymer—modified halloysite composite nanotubes." Journal of Applied Polymer Science 110.6 (2008): 3638-3646.
Guo, Baochun, et al. "Structure and performance of polyamide 6/halloysite nanotubes nanocomposites." Polymer journal 41.10 (2009): 835-842.
Du, Mingliang, Baochun Guo, and Demin Jia. "Newly emerging applications of halloysite nanotubes: a review." Polymer International 59.5 (2010): 574-582.

(Continued)

*Primary Examiner* — Mark Shibuya
*Assistant Examiner* — Yih-Horng Shiao
(74) *Attorney, Agent, or Firm* — Jones Walker LLP

(57) ABSTRACT

An augmented ceramic composite including aluminosilicate nanotubes may be added to a biocompatible polymer matrix. Aluminosilicate nanotubes have a surprisingly high biocompatibility, radio opaqueness, and suitability for storing therapeutic compounds for release over time. These surprising advantages make aluminosilicate nanotubes, such as halloysite nanotubes, a good candidate for use in various medical applications from bone and dental prosthetics to cancer treatment and prevention. Furthermore, unlike other additives, the addition of certain quantities of halloysite nanotubes increases the strength of the polymer matrix to which it is added.

20 Claims, 11 Drawing Sheets

(56) References Cited

OTHER PUBLICATIONS

Ward, Christopher J., Shang Song, and Edward W. Davis. "Controlled Release of Tetracycline-HCl from Halloysite-Polymer Composite Films." Journal of Nanoscience and Nanotechnology 10.10 (2010): 6641-6649.

Veerabadran, Nalinkanth G., Ronald R. Price, and Yuri M. Lvov. "Clay nanotubes for encapsulation and sustained release of drugs." Nano 2.02 (2007): 115-120.

Liu, Mingxian, et al. "The Role of Interactions between Halloysite Nanotubes and 2, 2'-(1, 2-Ethenediyldi-4, 1-phenylene) Bisbenzoxazole in Halloysite Reinforced Polypropylene Composites." Polymer journal 40.11 (2008): 1087-1093.

R. Price, BP Gaber, Y. Lvov, R. "In-vitro release characteristics of tetracycline HCl, khellin and nicotinamide adenine dineculeotide from halloysite; a cylindrical mineral." Journal of microencapsulation 18.6 (2001): 713-722.

Liu, Mingxian, et al. "Interactions between halloysite nanotubes and 2, 5-bis (2-benzoxazolyl) thiophene and their effects on reinforcement of polypropylene/halloysite nanocomposites." Nanotechnology 19.20 (2008): 205709.

Kuhn, K. D. "Chapter 3. 1: Properties of Bone Cement—What is Bone Cement? The well-cemented total hip arthroplasty: theory and practice." Heidelberg:Springer MedizinVerlag (2005): 52-59.

Fix, Dmitri, et al. "Application of Inhibitor—Loaded Halloysite Nanotubes in Active Anti-Corrosive Coatings." Advanced Functional Materials 19.11 (2009): 1720-1727.

Ismail, H., et al. "Morphological, thermal and tensile properties of halloysite nanotubes filled ethylene propylene diene monomer (EPDM) nanocomposites." Polymer Testing 27.7 (2008): 841-850.

Kommireddy, Dinesh S., et al. "Nanoparticle multilayers: Surface modification for cell attachment and growth." Journal of Biomedical Nanotechnology 1.3 (2005): 286-290.

Lvov, Yuri M., and Ronald R. Price. "Halloysite nanotubules, a novel substrate for the controlled delivery of bioactive molecules." Bioinorganic Hybrid Nanomaterials: Strategies, Syntheses, Characterization and Applications (2008): 419-441.

Tarì, Giuliano, et al. "Modification of surface charge properties during kaolinite to halloysite-7Å transformation." Journal of colloid and interface science 210.2 (1999): 360-366.

Lvov, Yuri, et al. "Thin film nanofabrication via layer-by-layer adsorption of tubule halloysite, spherical silica, proteins and polycations." Colloids and Surfaces A: Physicochemical and Engineering Aspects 198 (2002): 375-382.

Fu, Yubin, Lide Zhang, and Jiyong Zheng. "In-situ deposition of Pd nanoparticles on tubular halloysite template for initiation of metallization." Journal of nanoscience and nanotechnology 5.4 (2005): 558-564.

Fu, Yubin, and Lide Zhang. "Deposition feature of Ni nanoparticles on halloysite template and magnetic properties of the composite." Journal of nanoscience and nanotechnology 5.7 (2005): 1113-1119.

Shchukin, Dmitry G., and Helmuth Möhwald. "Surface—Engineered Nanocontainers for Entrapment of Corrosion Inhibitors." Advanced Functional Materials 17.9 (2007): 1451-1458.

Webb, J. C. J., and R. F. Spencer. "The role of polymethylmethacrylate bone cement in modern orthopaedic surgery." Journal of Bone & Joint Surgery, British vol. 89.7 (2007): 851-857.

Thornes, B., P. Murray, and D. Bouchier-Hayes. "Development of resistant strains of *Staphylococcus epidermidis* on gentamicin-loaded bone cement in vivo." Journal of Bone & Joint Surgery, British vol. 84.5 (2002): 758-760.

McGraw, J. Kevin, et al. "Prospective evaluation of pain relief in 100 patients undergoing percutaneous vertebroplasty: results and follow-up." Journal of vascular and interventional radiology 13.9 (2002): 883-886.

Fu, Yubin, and Lide Zhang. "Simultaneous deposition of Ni nanoparticles and wires on a tubular halloysite template: A novel metallized ceramic microstructure." Journal of Solid State Chemistry 178.11 (2005): 3595-3600.

Kommireddy, Dinesh S., et al. "Stem cell attachment to layer-by-layer assembled TiO< sub> 2</sub> nanoparticle thin films." Biomaterials 27.24 (2006): 4296-4303.

Shaik, J., et al. "In vitro evaluation of chondrosarcoma cells and canine chondrocytes on layer-by-layer (LbL) self-assembled multilayer nanofilms." Biofabrication 5 (2013): 1-9.

\* cited by examiner

PMMA

10%halloysite-PMMA composite 1.5% gentamicin

Cow bone cross section
Bone cement applied here

FIG. 2A        FIG. 2B        FIG. 2C
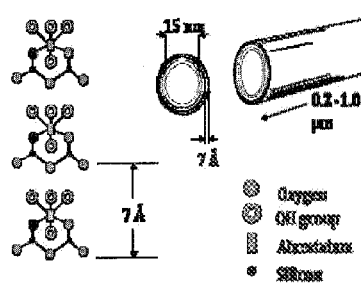 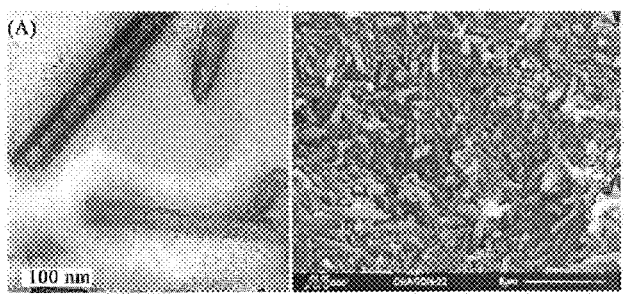

FIG. 6A  0% halloysite  FIG. 6B
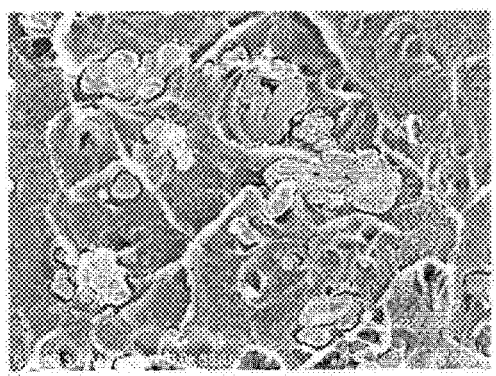 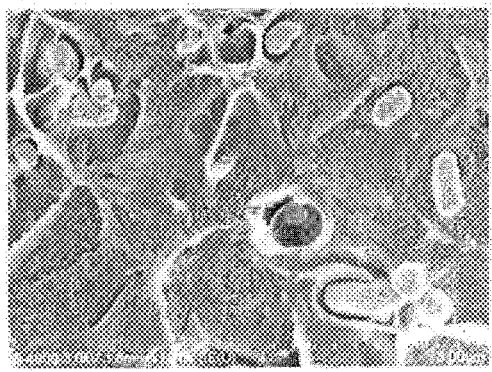
1.5% free gentamicin
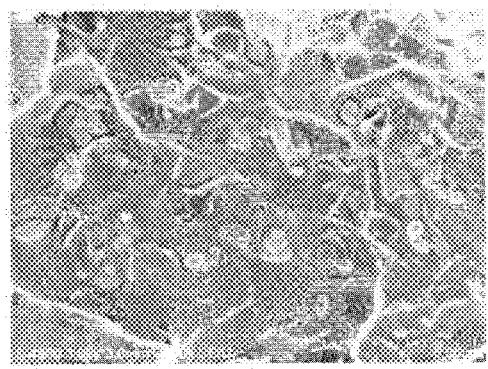 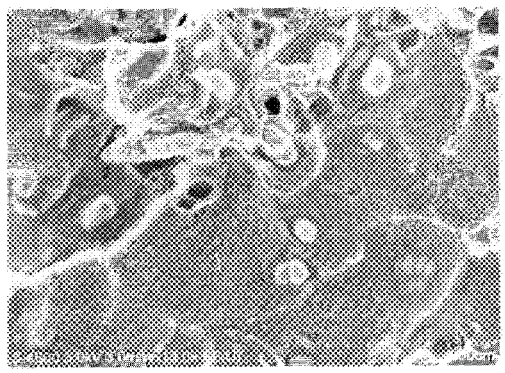
FIG. 6C  FIG. 6D FIG. 6E
5% halloysite
FIG. 6F
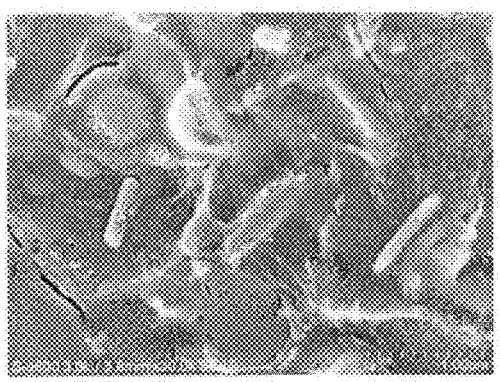
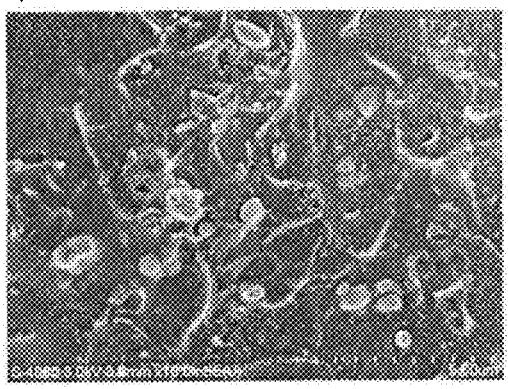
7.5% halloysite
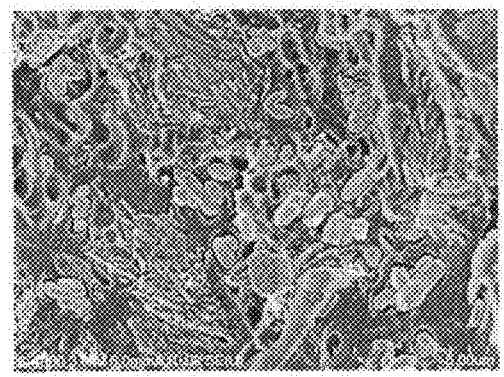
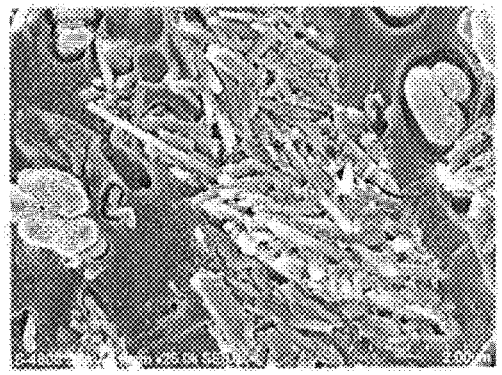
FIG. 6G
FIG. 6H FIG. 6I
10% halloysite
FIG. 6J
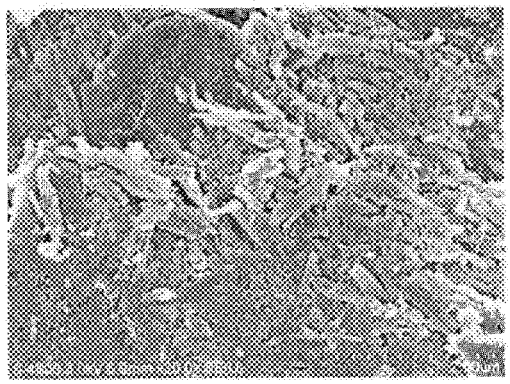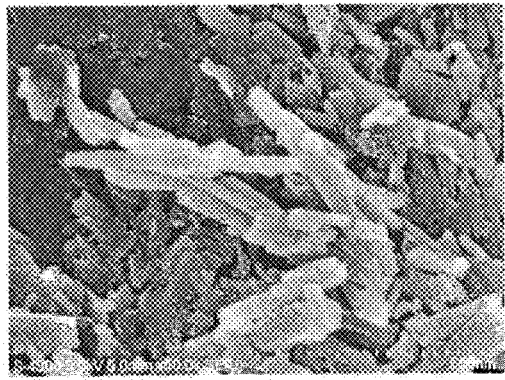
Bovine cortical bone
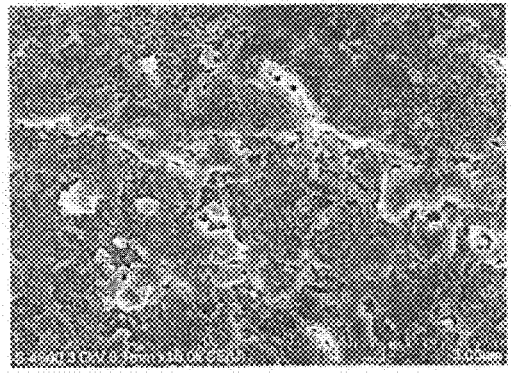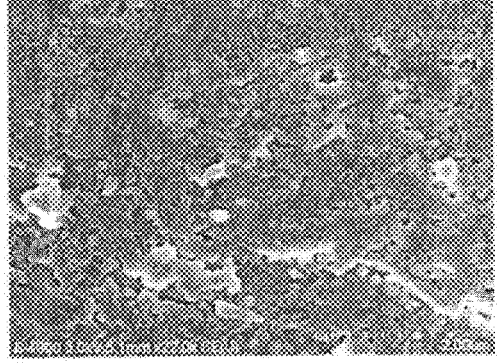
FIG. 6K
FIG. 6L

FIG. 9
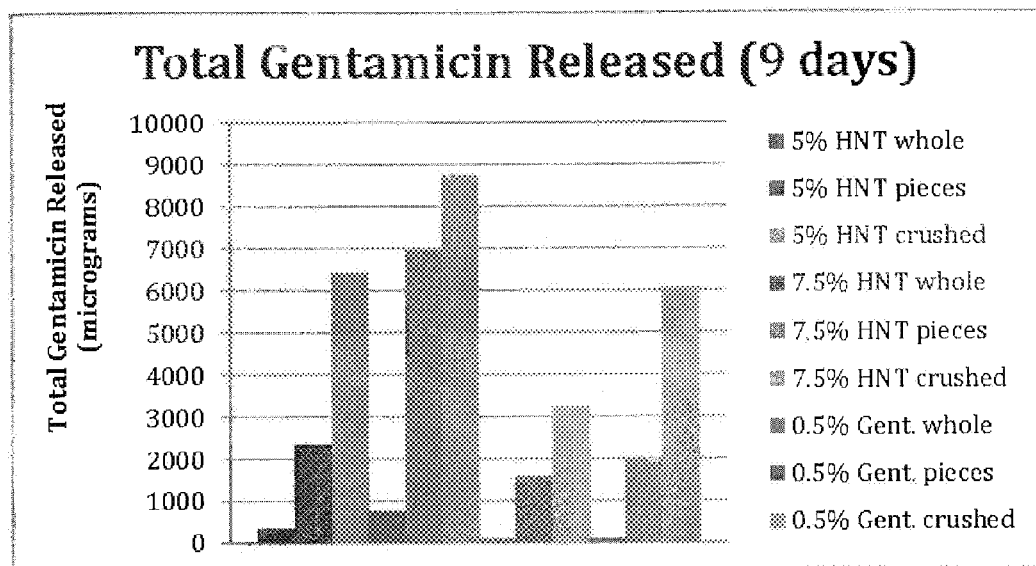
Fig. 6 b
FIG. 10
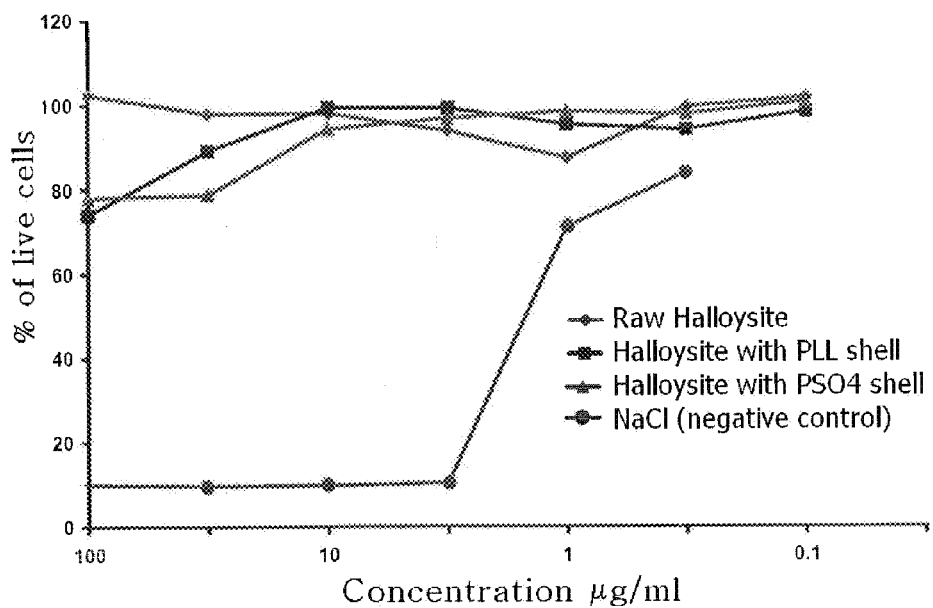

CERAMIC NANOTUBE COMPOSITES WITH SUSTAINED DRUG RELEASE CAPABILITY FOR IMPLANTS, BONE REPAIR AND REGENERATION

CROSS-REFERENCE TO RELATED APPLICATION

This application claims the benefit of U.S. Provisional Application No. 61/475,016, filed Apr. 13, 2011, which is hereby incorporated by reference.

STATEMENT REGARDING FEDERALLY SPONSORED RESEARCH OR DEVELOPMENT

This invention was made with government support under NSF-1029147 awarded by the Nation Science Foundation. The government has certain rights in the invention.

BACKGROUND

This present invention relates to ceramic nanotubes composites, in general augmented polymethylmethacrylate use in medicine or dentistry as a bone cement, dental restoration or other type of medical or dental prosthesis and methods of manufacture or use.

Bone cement is generally composed of a material known as polymethylmethacrylate (PMMA), and has been used by orthopedic surgeons for more than six decades. The first use of bone PMMA cement was in 1958 when British orthopedic surgeon Sir John Charnley implanted a hip endoprosthesis using PMMA. PMMA allows for the implantation and fixation of prostheses to the bone and has been the subject to continuous development in parallel with improvements of surgical techniques.

Bone cement tends to be a compound consisting of 90% PMMA. The remaining material is mainly crystals of barium or zirconium oxide that make the resulting product radio-opaque. The microscopic structure of bone cement consists of two substances glued together. One substance consists of pre-polymerized PMMA, supplied as "pearls." These "pearls" are supplied as a white powder. The preparation of bone cement involves mixing powdered PMMA (the "pearl" mixture) with a liquid containing monomeric methylmethacrylate (MMA) in the presence of a catalyst. The powder quickly dissolves in the monomer and undergoes a polymerization reaction at room temperature to form putty-like cement. The polymerizing fluid glues together the pearls into a firm, strong, but brittle mass. When the liquid monomer polymerizes and the bone cement hardens, the individual pearls are entrapped and glued within a net of the polymerized monomer. There is no chemical binding, however, between the pearls and the polymerized monomer.

The term cement in this field may be a misnomer. Most often the word cement is used to describe something that adheres, or sticks together, two substances or materials. Cement implies that the material sticks the implant into the bone. Bone cement acts not as a glue but as a filler, like grout. It is added during surgery. The reason is that this material acts as a space-filler. It fills the void between the implant and surrounding bone by creating a tight space for the implant to be held firmly against the bone. Plexiglas® or Lucite® are materials that consist of nearly pure PMMA. Plexiglas® is one of the strongest plastics.

Bone Cements for primary arthroplasty are in widespread use by orthopedists and other surgeons. Bone cement is a substance commonly used for fixation of artificial joints in bone and is extensively used in hip and knee replacement surgery. Various types of bone cements are available to surgeons that vary in regard to viscosity, processing, content, and application properties.

Many surgeons mix prophylactic antibiotics into the bone cement while mixing the components together. Many types of antibiotics can be used in the mixing process, the typical antibiotics used consist of gentamicin, tobramycin or vancomycin. Worldwide tobramycin is very commonly used. Gentamicin and tobramycin are an aminoglycoside antibiotic used to treat various types of bacterial infections, particularly Gram-negative infections. Vancomycin is a glycopeptides antibiotic used in the prophylaxis and treatment of infections caused by Gram-positive bacteria. Surgeons in the United States predominantly use gentamicin. These antibiotics are available in a powdered form that can easily be mixed into the PMMA. Once PMMA is mixed with antibiotics and used in a procedure the antibiotics will leak from the bone cement into the surrounding areas. The local concentration of antibiotics is usually sufficient to initially kill the bacteria left in the operative wound.

However, addition of antibiotics to bone cement leads to a weakening of the cement. It has been demonstrated that addition of antibiotics to bone cement leads to a loss of mechanical strength. There is also limited sustained release of the antibiotics from the PMMA over a longer time period. This limited release could be only 3%-5% of the loaded antibiotics. Mixing the antibiotics in uniformly can be difficult even when done with a sonicator. PMMA is not a porous material. Close to 70 percent of the antibiotics which are released are released within the first 24 hours in standard commercially viable bone cements. This release also only constitutes a low percentage of the total available antibiotic. The non-porous nature of PMMA bone cement causes limited release of the antibiotics that are widely (and unevenly) distributed throughout the cement sample.

What is needed is a bone cement that has been augmented with a biocompatible material that can both add strength to prevent mechanical failure, significantly increase adhesion and also act to provide a sustained release of a substance of interest.

The disclosure allows for a novel bone cement material that can have improved material strength, adhesiveness and delivery properties.

SUMMARY

One embodiment includes an augmented ceramic composite, comprising halloysite nanotubes thoroughly disaggregated and uniformly dispersed in a ceramic matrix for dental and medical applications.

Another embodiment includes the hollow spaces in the halloysite nanotubes comprising quantities of beneficial pharmaceutically effective compositions selected from a group consisting of antibiotics, anti-inflammatories, chemotherapeutic agents, bone growth promoting agents, imaging agents and any mixtures thereof.

Other aspects and advantages will become apparent upon consideration of the following detailed description and the attached drawings, in which like elements are assigned like reference numerals.

BRIEF DESCRIPTION OF THE DRAWINGS

FIGS. 2A-C show halloysite as it occurs in nature as a hydrated mineral having the formula $Al_2Si_2O_5(OH)_4.2H_2O$, which is similar to kaolinite except for the presence of an additional water monolayer between the adjacent layers. It forms by kaolinite layer rolling due to the action of hydrothermal processes. FIG. 2A shows a sketch of halloysite nanotubes. FIGS. 2B and 2C shows halloysite clay comprising tubular nanoparticles of ca 50 nm external diameter, 15 nm luminal diameter and 500-1500 nm in length.

FIG. 3 is a graph showing tensile strength test results. All samples were made into bone shape much like a dog bone and each sample weighed 5±0.5 g. The center part of each sample is 3 cm (Length)×1 cm (Width)×0.5 cm (Thickness) All samples were placed in water for 15 days before each test. Samples were pulled with tensile tester until they broke. This graph shows the release profiles of unloaded halloysite nanotubes compared to gentamicin and in combination with gentamicin mixed in.

FIG. 6 A-L show photographs from a scanning electron microscope observing a halloysite/PMMA composite and bovine bone. FIG. 6A & FIG. 6B show no halloysite addition to PMMA. FIG. 6C and FIG. 6D show a 1.5% halloysite nanotubes addition to PMMA. FIG. 6E and FIG. 6F show a 5% halloysite addition to PMMA. FIG. 6G and FIG. 6H show a 7.5% halloysite addition to PMMA. FIG. 6I and FIG. 6J show a 10% halloysite addition to PMMA. FIG. 6K and FIG. 6L bovine cortical bone.

FIG. 9 is a bar graph showing total gentamicin released (9 days).

FIG. 10 is a line graph showing concentration (μg/ml) versus % of live cells.

DESCRIPTION

Figure 1A:
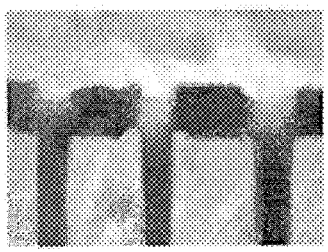
FIGS. 1A-C show pictures of samples after adhesion testing. Maximum displacement force for the cement with 10% halloysite loaded with gentamicin (FIG. 1B) was 500±20 N, while maximum displacement force for the pure cement (FIG. 1A) and cement with 1.5% free gentamicin (FIG. 1C) were 290±20 and 280±80 N.
Figure 1B:
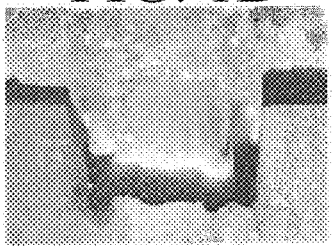
Figure 1C:
Figure 1D:
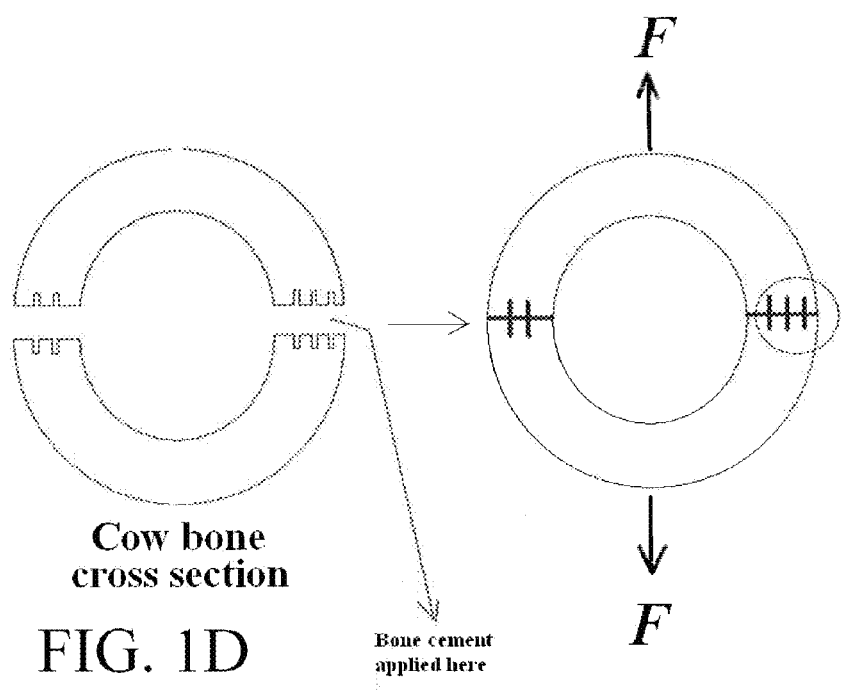
FIG. 1D shows a cross section of a cow bone as said forces were applied to it. This testing shows a drastic increase in the strength of the nanocomposite compared to a standard PMMA or PMMA with a gentamicin additive.

This disclosure generally relates to mechanisms of augmenting bone cement that add mechanical strength and a sustained release profile of a substance of interest using halloysite nanotubes. This present invention relates to ceramic nanotubes composites or synthetic resins, in general augmented polymethylmethacrylate, used in medicine or dentistry as a bone cement, dental restoration or other type of medical or dental prosthesis and methods of manufacture or use. The resin may also include or incorporate any appropriate inhibitor, promoter or accelerator, stabilizer, initiator, catalyst, radiopacifier and/or radiopaquing agent of a type known in the art.

Halloysite is a biocompatible and economically viable clay material that can be mined from deposits as a raw material. Halloysite ($Al_2Si_2O_5(OH)_4 \times nH_2O$) is a two layered (1:1) aluminosilicate chemically similar to kaolin, which inhabits a range of morphologies. One predominant form is a hollow tubular structure in the sub micrometer range. The reason flat kaolinite roles into halloysite tubules remains unclear.

Halloysite nanotubes are able to give a greater mechanical strength to PMMA, significantly increase adhesiveness to surrounding materials as well as act as ceramic tubular nanocontainers for sustained release of drugs or other beneficial compounds.

Such nanotubes being admixed into PMMA bone cement or equivalent materials will provide slower and more sustained release profiles. An example of this is a sustained release of gentamicin that could last 10-100 hours or even a 240 hour release profiles. See FIG. 7. In standard antibiotic bone cements there is an initial spike or release burst of the mixed in antibiotic. After this point the release drastically decreases. The halloysite loaded nanotubules have a more sustained release profile. Additionally, halloysite can be targeted with an ultrasonic device such as a standard ultra-sound machine to cause a targeted spike or release.

Drugs or proteins loaded into the nanotubes are protected from deterioration by the cement components and exothermic reaction. Therefore, drugs loaded in this ceramic nanotube will not be admixed with the implant bulk polymer and the strength of the bone cement will not deteriorate as in the case of the simple addition of non-encapsulated gentamicin.

This concept covers not only nanotube encasing of gentamicin, but other medicine and proteins which will enable slow release from such nanocomposites of halloysite and bone cement. Using a "palette" of halloysite nanocarriers loaded with different drugs or substances of interest for "a la carte" admixing to bone cement with adjustment to the patient needs is possible.

Halloysite nanotubes include hollow spaces capable of carrying minute quantities of pharmaceutically beneficial compositions. Such compositions may, for example, be selected from a group consisting of small sized antibiotics, anti-inflammatories, chemotherapeutic agents, bone growth promoting agents, compounds that aide in the imaging of bone cement or a joint such as contrasting agents, therapeutic agents and any mixtures thereof. The loading of the hollow spaces in the nanotubes with appropriately sized antibiotic drugs or other agents to treat infection should function at the site as a prophylactic to address this problem. Bone growth promoters (osteo-inductive and osteo-conductive) as well as other desired proteins and agents function to provide site effective measures to enhance the bonding of the implant to the surrounding bone.

The term "therapeutic agents" as used herein is to be broadly construed to include any feasible drugs, prodrugs, proteins, diagnostic agents, pain killers, PH buffering compounds, contrast or imaging agents. For example, in some applications where it is desired to treat or prevent a microbial infection, the substance delivered may comprise pharmaceutically acceptable salt or dosage form of an antimicrobial agent (e.g., antibiotic, antiviral, antiparacytic, antifungal, etc.), a corticosteroid or other anti-inflammatory (e.g., an NSAID), a vasoconstrictor or vasodilator, an agent that prevents of modifies an allergic response (e.g., an antihistamine, cytokine inhibitor, leucotriene inhibitor, IgE inhibitor, immunomodulator), etc. Several of these substances are detailed within this application and other documents such as U.S. Pat. Nos. 7,361,168 and 7,833,270, where are incorporated by reference.

Some nonlimiting examples of antimicrobial agents that may be used in this invention include acyclovir, amantadine, aminoglycosides (e.g., amikacin, gentamicin and tobramycin), amoxicillin, amoxicillin/clavulanate, amphotericin B, ampicillin, ampicillin/sulbactam, atovaquone, azithromycin, cefazolin, cefepime, cefotaxime, cefotetan, cefpodoxime, ceftazidime, ceftizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscarnet, ganciclovir, atifloxacin, imipenem/cilastatin, isoniazid, itraconazole, ketoconazole, metronidazole, nafcillin, nafcillin, nystatin, penicillin, penicillin G, pentamidine, piperacillin/tazobactam, rifampin, quinupristin-dalfopristin, ticarcillin/clavulanate, trimethoprim/sulfamethoxazole, valacyclovir, vancomycin, mafenide, silver sulfadiazine, mupirocin, nystatin, triamcinolone/nystatin, clotrimazole/betamethasone, clotrimazole, ketoconazole, butoconazole, miconazole, tioconazole, antiretroviral agents, genetically engineered or naturally occurring antibodies, antimicrobial proteins or peptides such as those described in U.S. Pat. No. 6,716,813, incorporated by reference, or antimicrobial metals (e.g., colloidal silver).

Additionally or alternatively, in some applications where it is desired to treat or prevent inflammation the substances delivered in this invention may include various steroids or other anti-inflammatory agents (e.g., nonsteroidal anti-inflammatory agents or NSAIDS), analgesic agents or antipyretic agents. Also, other non-limiting examples of steroids that may be useable in the present invention include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexamethasone and methylprednisolone. Other anti-inflammatory, analgesic or antipyretic agents that may be used include the nonselective COX inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2 Inhibitors (e.g., diaryl-substituted furanones such as rofecoxib; diaryl-substituted pyrazoles such as celecoxib; indole acetic acids such as etodolac and sulfonanilides such as nimesulide).

Additionally or alternatively, in some applications, such as those where it is desired to treat or prevent an allergic or immune response and/or cellular proliferation, the substances delivered in this invention may include various cytokine inhibitors such as humanized anti-cytokine antibodies, and anti-cytokine receptor antibodies.

Additionally or alternatively, in some applications, such as those where it is desired to effect angiogenesis by promoters or inhibitors some non-limiting examples are FGF, VEGF, VEGFR, NRP-1, Ang1, Ang2, PDGF (BB-homodimer), PDGFR, TGF-β, endoglin, TGF-β, MCP-1, Integrins αVβ3, αVβ5, α5β1, VE-cadherin, CD31, ephrin, plasminogen, eNOS, COX-2, AC133, and Id1/Id3. In terms of hemostasis, the substances delivered in this invention may include various vasoconstrictors or vasodilators.

Additionally or alternatively, in some applications such as those where it is desired to prevent or deter histamine release, the substances delivered in this invention may include various mast cell stabilizers or drugs which prevent the release of histamine such as cromolyn (e.g., Nasal Chrom®) and nedocromil. In one particular embodiment, the substance delivered by this invention could comprise a combination of an anti-inflammatory agent (e.g. a steroid or an NSAID). The substances delivered in this invention may include various antihistamines such as azelastine (e.g., Astylin®), diphenhydramine, loratidine, etc.

Additionally or alternatively, in some applications such as those wherein it is desired to treat a tumor or cancerous lesion, the substances delivered in this invention may include antitumor agents (e.g., cancer chemotherapeutic agents, biological response modifiers, vascularization inhibitors, hormone receptor blockers, cryotherapeutic agents or other agents that destroy or inhibit neoplasia or tumorigenesis), including: alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase ingibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000), incorporated by reference, biological response modifiers (e.g., interferon, bacillus calmette-guerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, flurouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogs/congeners and derivatives of such compounds as well as other antitumor agents not listed here.

Additionally or alternatively, in some applications such as those where it is desired to have bone growth that include but are not limited to bone morphogenic proteins, for example, BMP-2, rhBMP-2, BMP-4, rhBMP-4, BMP-6, rhBMP-6, BMP-7 [OP-1], rhBMP-7, GDF-5, and rhGDF-5, as disclosed, for example, in the U.S. Pat. Nos. 4,877,864; 5,013,649; 5,661,007; 5,688,678; 6,177,406; 6,432,919; 6,534,268; and 6,858,431, and in Wozney, J. M., et al. (1988) Science, 242(4885):1528-1534, each of which are incorporated by reference. Bone morphogenic proteins have been shown to be excellent at growing bone and there are several products being tested. Extensive animal testing has already been undertaken, and human trials are finished and in process for these products. Studies with these and other BMP's are underway.

Additionally, suitable growth factors include, without limitation, LIM mineralization protein, platelet derived growth factor (PDGF), transforming growth factor .beta. (TGF-.beta.), insulin-related growth factor-I (IGF-I), insulin-related growth factor-II (IGF-II), fibroblast growth factor (FGF), and beta-2-microglobulin (BDGF II), as disclosed in the U.S. Pat. No. 6,630,153, incorporated by reference, and PTH, PGE2-aganonist, and statins.

Additionally, some example of bone cement contrast agents which allow for MRI imaging of bone cement by making the substance radiopaque include zirconium dioxide (ZrO2), barium sulphate (BaSO4), gadolinium in gadoterate meglumine and manganese (MnC12). Other newly developing agents such as bismuth should be noted.

Additionally coloring agents such as Chlorophyll can be added to aide in identification of bone cement to during revisions.

TEM, SEM and SFM microscopy have characterized halloysite clay as tubular nanoparticles of ca 50 nm external diameter, 15 nm luminal diameter and 500-1500 nm in length. In a wide range of pH, it has a negative electrical zeta-potential of ca-50 mV, which allows halloysite good dispensability in water-based polymers and other media (including melted polymers) (See FIGS. 2B and 2C). An addition of halloysite nanotubes to four different cell line cultures demonstrated that it is nontoxic up to concentrations of 0.1 mg/mL. This suggests that halloysite nanotubes are not toxic and are excellent candidates for use as nanocontainers for medical devices, bio-coatings or implants.

The material properties of a ceramic nanocomposite with halloysite nanotubes vary in relation to the percent weight of halloysite nanotubes to the nanocomposite. Tests have shown that halloysite nanotubes added to PMMA have a preferred material strength at percent weights from 7%-10%. It must be noted that percentages as lows as 0.005% and as high as 20% can be beneficial in specific scenarios. For example a 7.5% added halloysite composition yielded a 30-40% strength increase during young modulus testing. An optimal composition depends upon the amount of a desired substance to be released and the strength increase that is desired. After a certain added percent weight, the material strength of the nanocomposite can begin to decrease.

Halloysite nanotubes, in addition to having a key role as a nanocarrier of instructional agents, also have great potential as enhancers of structural integrity in such hard tissues as bone and enamel. The benefit of improved physical properties is associated with and can be applied to bone tissue engineering and repair (increases in tensile strength), increasing the wear increasing the wear resistance and material properties of dental composites, restorations and anti-infective biocoatings. Furthermore, the addition of halloysite makes bone cement radio-opaque, an important property for orthopedic surgeons. Halloysite has significant potential as a sustained molecular delivery mechanism and with its ability to reinforce dental increasing the wear resistance and material properties of dental ability to reinforce dental and skeletal tissues it holds great promise for applications in other tissues.

Bone cement under pressure can be injected into fractured vertebrae, typically with a catheter. Bones are the third most common location where cancer cells spread and metastasize. Each year, about 100,000 cases of bone metastasis are reported in the United States. If left untreated, bone metastases can eventually cause the bone to fracture—seriously affecting a patient's quality of life. This is particularly true for long bones of the extremities where a fracture may render a limb nonfunctional. These patients may require surgical intervention to restore the function of their limbs. More commonly, metastases involve the ribs, pelvis, and spine. Bone cement may also be used to hold a device such as a catheter in place in the body.

Halloysite has several advantages over the existing competitor technology, carbon nanotubes. In contrast, to carbon nanotubes, it is significantly cheaper, does not provoke a cytotoxic cellular response, has broad applicability in the medical device and dental and orthopedic fields, and is tunable to meet specific patient needs.

Biocompatibility is the ability of a material to perform with an appropriate host response in a specific application. Also biocompatibility means that the material does not have toxic or injurious effects on biological systems. Biocompatibility is the capability of a prosthesis implanted in the body to exist in harmony with tissue without causing deleterious changes. A limited biocompatible material could be thought of as carbon nanotubes which have toxic effects on their host.

The controlled release capabilities of halloysite nanotubes afford multiple applications including but not limited to sustained release of: 1] antibiotics from bone cement, 2] growth factors for dental and orthopedic implants, 3] release of anti-infective agents as implant biocoatings, 4] prevention of bacterial biofilm formation and therefore postsurgical infection, and 5] release of instructional biomolecules from soft tissue implants or dressings (e.g., poly-e-caprolactone or bone morphogenic protein). In addition, halloysite nanotubes possess the ability to reinforce bone cement and the increase the material strength and wear properties of bone cement and dental composites, implants and restorations.

The strength of the halloysite and bone interaction is increased due to rough surfaces that are created when adding halloysite to the bone cement. In normal bone cement the surface tends to dry in a smooth nonporous surface, with the addition of small halloysite nanotubes this smooth surface is altered to be porous. This porous surface creates places for new osteoblasts to grow and build a matrix that increases the bone to cement strength, such as when cement is poured into a rebar matrix.

Halloysite nanotubes, have an average nano-confined luminal volume of about 15-nm diameter (See FIGS. 2A-C). Among other templates studied for biomineralization, halloysite, a naturally occurring aluminosilicate nanotubes, has been underservedly overlooked. A halloysite nanotube is defined as a two-layered aluminosilicate that has predominantly hollow tubular structures in the submicron range. In many embodiments, halloysite nanotubes are chemically similar to kaolin. The neighboring aluminum and silica layers and their waters of hydration create a packing disorder causing them to curve. Halloysite is an economically viable raw material that can be mined from the corresponding deposit as a raw mineral. As for most natural materials, the size of halloysite particles varies within 1-2 microns of length and 15-50 nm of inner diameter depending on the deposits. Almost all varieties of halloysite tubules can be added to make nanocomposites and sizes can be chosen for specific material properties and results. Halloysite nanotubes are capable of entrapping a range of active agents within the inner lumen, followed by their retention and slow release.

A substantial amount of current research activity is devoted to carbon nanotubes. As for other tubular materials, there are also polymeric, metal, and metal oxide nanotubes. Polymeric nanotubes can be formed by self-assembly in some cases, or templated by molecular sieves or cylindrical nanopores to form tubular structures. Metal and metal oxide nanotubes are synthesized predominantly by a template method using polymeric or inorganic nano-rods, which have to be prepared separately, as a template scaffold. The disadvantage of these types of nanotubes is the employment of a template, which has to be removed after synthesis of the tubes, leading to low quantities of the product, time consuming preparation procedures (including the preparation of the template itself), and limits on scalability for commercial applications. The lumen diameter of halloysite tubes ideally fits to globular protein diameters, allowing the incasing in the tube and feeding them with low molecular compounds for biocatalysis.

In a bone cement composite system, Halloysite nanotubes were loaded with the antibiotic, gentamicin sulfate with loading efficiency of 10%/wt, permitting increases in the amount of loaded antibiotic, and greater elution profiles with no reduction in the material properties of the halloysite-reinforced bone cement. The data showed a significant increase in gentamicin sulfate release times when vacuum loaded into Halloysite nanotubes. Additionally, tensile strength was increased (see FIG. 3) with no detriment to cell proliferation and protein synthesis in vitro.

Figure 7:
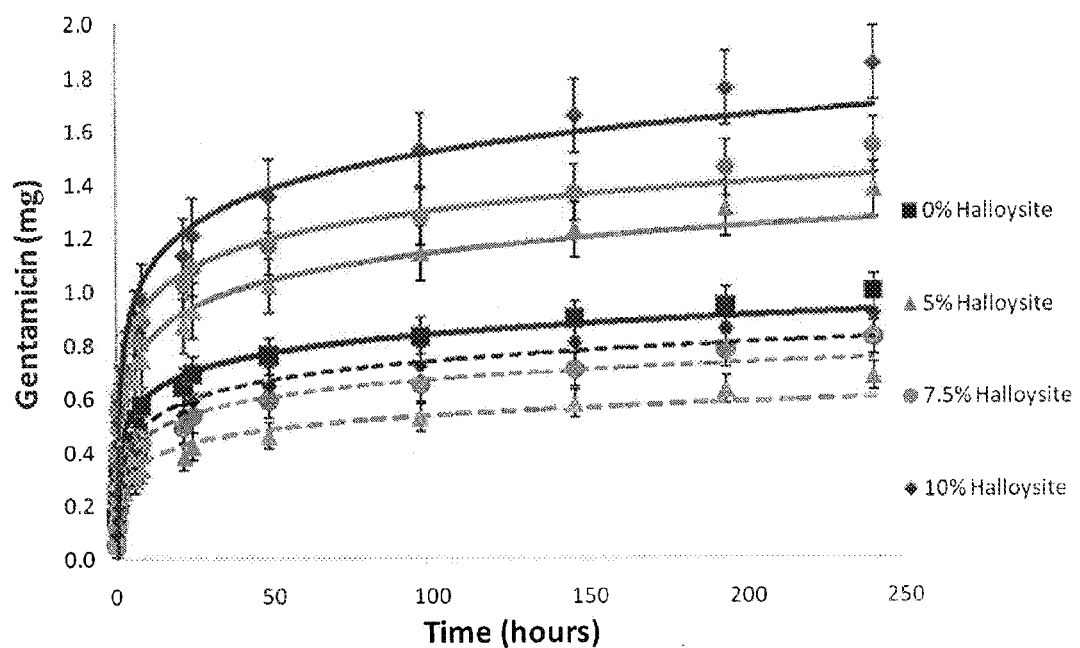
FIG. 7 is a graph showing gentamicin release after 240 hours. The solid lines contain 1.5% wt free gentamicin, and the broken lines only contain loaded halloysite. Each sample is 150±10 mg. The 240 hour or 10 day release profile is likely to have extended after the 10 day mark. Crush testing later on showed that halloysite nanotubes still had the loaded antibiotics and could have continued a release profile.
Figure 8:
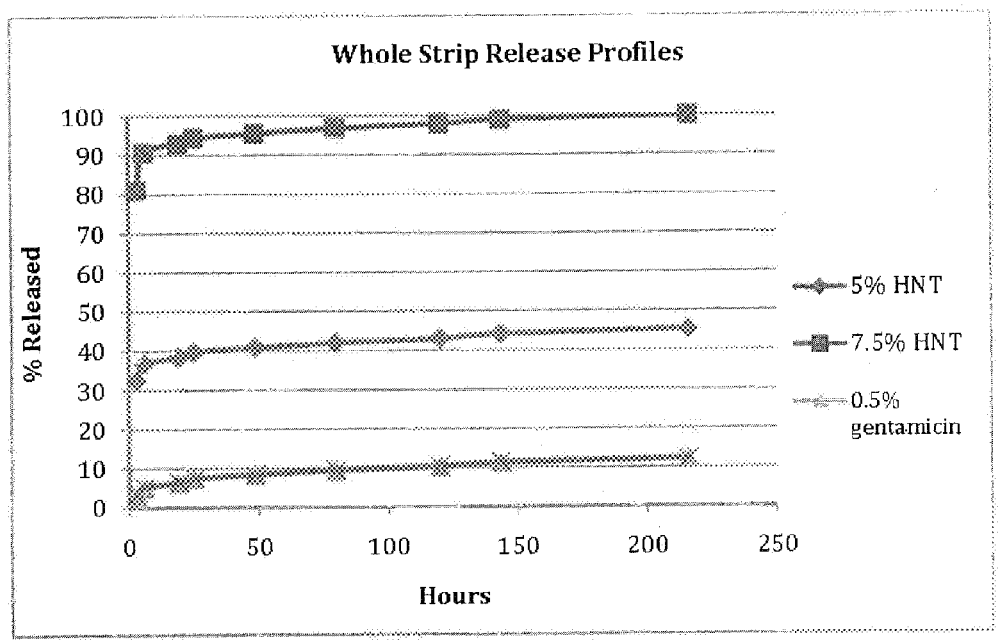
FIG. 8 is a line graph showing whole strip release profiles.

Halloysite loaded with Gentamicin was admixed to PMMA bone cement at 1, 5, and 7.5% weight. This should just be the percentage of weight of the final material that the loaded halloysite constitutes. The composite was dried and then released and analyzed. These composites demonstrated extended release time, with total release over the course of 100 hours. Release curves from composites do with gentamicin loaded halloysite are shown in FIG. 7. The initial burst has to be subtracted because the tubes were not washed from gentamicin before composite preparation. One can see essentially longer release time as compared with release from "pure" halloysite tubes.

Antibiotic-loaded bone cement (ABLC) has been in use for over 30 years. It is thought that the antibiotic eludes into the area of the wound from the bone cement with which it has been mixed, thus reducing the incidence of implant infection, a major concern in joint replacement. While rare, infection of total joint arthoplasty can be a devastating complication, resulting in significant patient discomfort, increased medical costs, and potential lawsuits.

It has been argued that the older approach of merely mixing antibiotics in commercial bone cement may have some limitations and mixing antibiotics intra-operatively into carefully composed bone cement presents certain risks—allergic reactions, cement mechanical failures, toxicity, and development of resistance. Halloysite nanotubes overcome many of these limitations.

Surgeons cannot be sure that the mechanical properties of the bone cement have not been compromised by standard antibiotic additives. Homogenous commercial mixing of an antibiotic in bone cement result in less mechanical strength. Antibiotics employed are not specifically targeted at the individual bacterial species prevalent in most hospital environments and that antibiotics in the bone cement may produce increased bacterial resistance. Additionally, the majority of antibiotics remain inside the bone cement.

Addition of antibiotic to bone cement leads to weakening of the cement. Disclosures by Heyse-Moore and Ling demonstrated that addition of antibiotics to bone cement leads to a loss of mechanical strength. Use of antibiotic-loaded cement reduces postoperative revision implant infection rates and is currently recommended for revision surgery. There is little long-term protection from infection after use of such cement.

In order to improve elution rates and diminish weakening the cement, we have developed a biocompatible nanocarrier with inherent capabilities (sustained biomolecule release, strengthened mechanical properties, increased wear resistance and adhesiveness, anti-infective properties), thereby paving the way for multiple applications in clinical and regenerative medicine. Halloysite nanotubes have an inherent ability to internalize low molecular-weight substances, such as proteins, antibiotics, growth factors, drugs, and anti-corrosion molecules, and by coating through layer-by-layer nanoassembly can be modified for various capabilities such as slow release of the above as well as for instructive and protective coatings of tubules, implant surfaces, dental composites and restorations while improving their natural material properties. In addition, halloysite nanotubes can also improve the surgical outcomes in bone and joint surgery leading to an improvement in patients' health-related quality of life, and develop and offer innovative anti-infective coatings for medical devices and implants. Furthermore, biomedical and clinical application of halloysite nanotubes may lead to a significant reduction in healthcare costs.

There are many commercial applications of this technology. A few non-limiting applications are joint replacements, treatment of infection and infected implants, Treatment of osteomyelitis, Dental implants, Dental composites and restorations, Anti-infective implant biocoatings and fracture management Experimental Overview The following examples serve to illustrate certain preferred embodiments and aspects of the present disclosures and are not to be construed as limiting the scope thereof.

Materials:

The PMMA cement, Orthoset 3 was provided by Wright Medical Technologies (Arlington, Tenn., USA) and used for testing. Halloysite nanotubes (HNT) were provided by Applied Minerals, Inc. (New York, N.Y., USA). Gentamicin sulfate 1 g units came from Cellgro by Mediatech Inc. (Manassas, Va., USA).

Sterilizing HNT:

There are many ways HNTs may be sterilized. Coated substrates may be immersed in a 75% ethanol solution and rinsed in Hank's balanced salt solution (HBSS) before plating with cells. Other sterilization methods include using irradiation and ethylene oxide.

Loading Antibiotics in HNT Lumen:

Powder halloysite nanotubes were introduced to a concentrated solution of gentamicin sulfate (50 mg/ml). The suspension was then sonicated for 2 hours, followed by 20 min in a vacuum at 100 torr. Vacuuming was done in three intervals, each 20 min long, with 10 minutes at atmospheric pressure between each vacuum session. After vacuuming supernatant was taken off the samples, and the remaining sample was put in an oven at 55° C. for 4 hours to dry. Samples were then either briefly washed to remove gentamicin associated with the outside surface of HNT or used immediately for testing with gentamicin still bound to the outside of the tubule.

Sample Preparation:

PMMA samples were made as per manufacturer instructions with slight modification to incorporate halloysite nanotubes or crystalline gentamicin. In a stainless steel mixing bowl, powder PMMA was mixed with the other dry reagents. Once dry reagents were mixed well, liquid MMA monomer solution was then added to start polymerization. At 8 minutes of mixing, a putty-like composite was put in a mold lined with aluminum foil. Samples were fully polymerized after 15 min and were removed from the mold.

O-Phthaldialdehyde Solution:

The solution was made by adding 2.5 g o-phthaldialdehyde (Sigma-Aldrich, St. Louis, Mo., USA), 62.5 ml methanol (Sigma-Aldrich, St. Louis, Mo., USA), 3 ml β-mercaptoethanol (Sigma-Aldrich, St. Louis, Mo., USA), and 560 ml 0.04M sodium borate. The solution was then allowed to sit at room temperature for 24 hrs before use. The solution was not used after 72 hrs.

Gentamicin Release:

Release experiments were conducted by putting samples, of carrying surfaces to volume ratios, in phosphate buffered saline (PBS). At each reading, liquid was taken off the samples and replaced with fresh PBS. To quantify gentamicin, equal parts fluid sample, isopropanol and o-phthaldialdehyde solution were put together and let sit at room temperature for 30 minutes. Using a spectrophotometer, samples were read at 331 nm wavelength.

Figure 3:
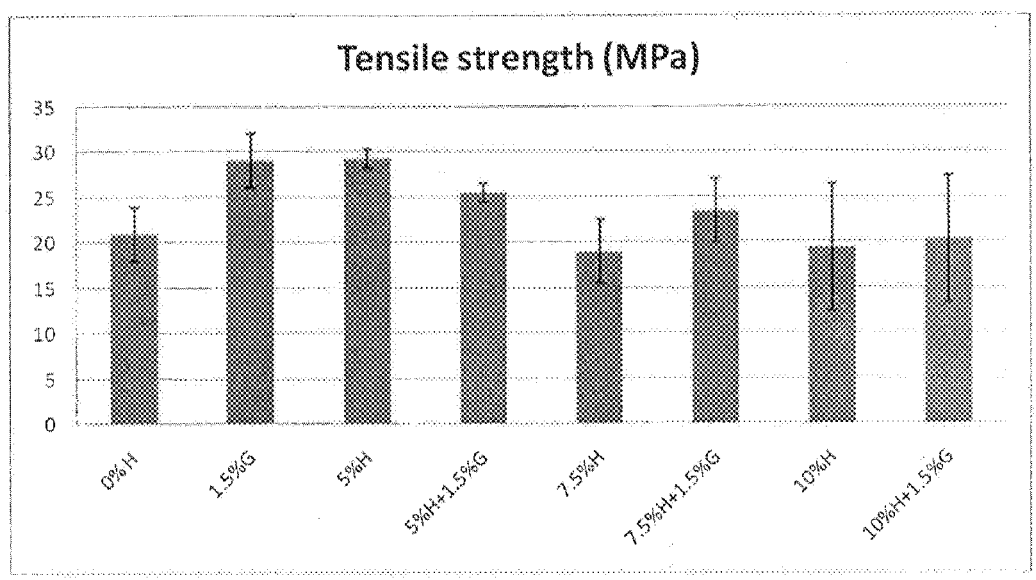
Figure 4:
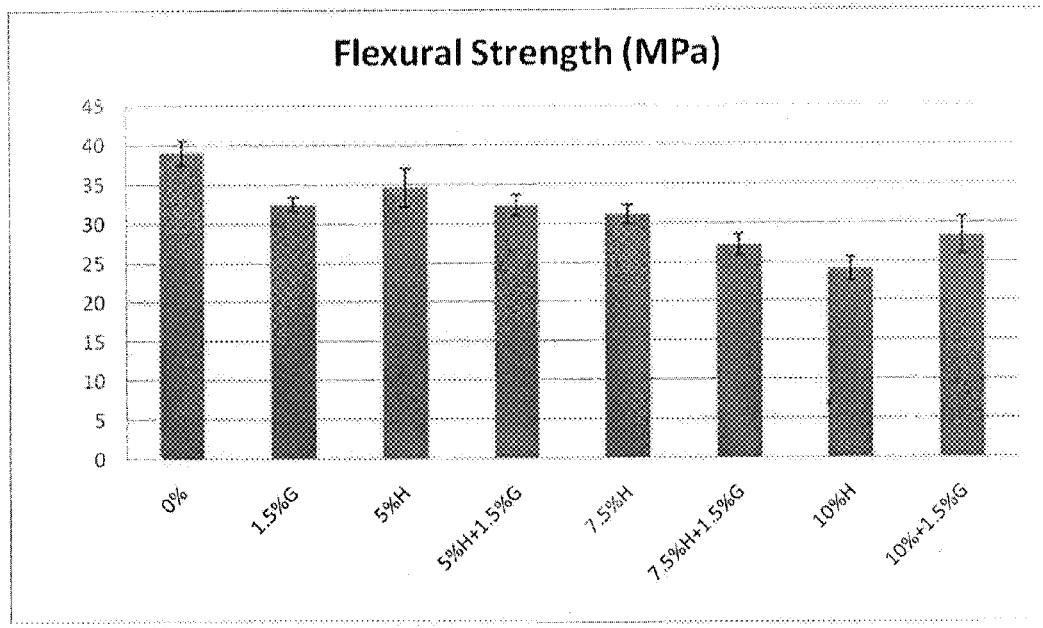
FIG. 4 is a graph showing flexural strength test results. All samples were formed into a rectangle shape with 2.5 cm (Length)×1 cm (Width)×0.3 cm (Thickness) and each weighed 3.0±0.5 g. Samples were placed in water for 2 days before test. Bend the samples from the central part to measure the maximum break force. Halloysite nanotubes were able to increase the strength of the composite and avoid loss of strength when high weight percentages of antibiotics were used.
Figure 5:
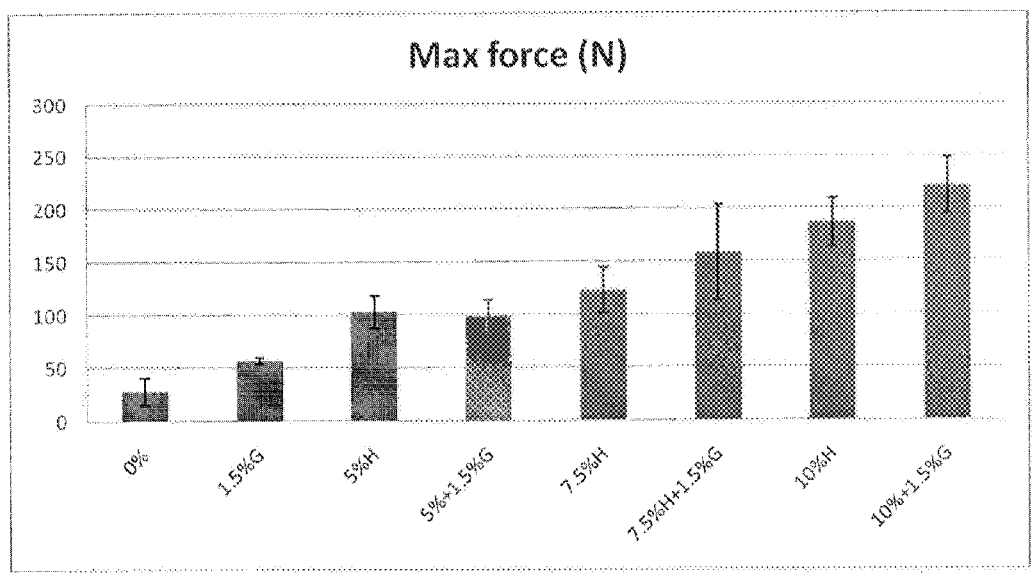
FIG. 5 is a graph showing adhesion test results for maximum force displacement. Samples were placed on the surfaces of bovine (diaphyseal) bone surfaces, the size of each samples was 1 cm×1 cm. 50-LB of compressive force was applied to depress the arm and measure the maximum force (N) required to remove the sample from the cow femur bone. The halloysite percent increases show a substantial increase in strength as HNT percent by weight goes up from zero to 10 percent.

Mechanical Testing:

Mechanical property tests of halloysite-PMMA composites can be done. An ADMET tensile strength machine was used to test samples tensile and flexural strength and adhesiveness on bovine cortical (femoral) bone (see FIGS. 3 and 4). All samples were made into a bone shape much like a dog bone and each sample weighed 5±0.5 g. The center part of each sample is 3 cm (Length)×1 cm (Width)×0.5 cm (Thickness). All samples were placed into water for 15 days before each test. Samples were pulled with tensile tester until they broke (FIG. 3). Flexural testing can also be done (FIG. 4). All samples were formed into a rectangle shape with 2.5 cm (Length)×1 cm (Width)×0.3 cm (Thickness) and each weighed 3.0±0.5 g. Samples were placed in water for 2 days before the test. Samples were bent from the central part to measure the maximum break force. Adhesion testing of mechanical properties can be done. Samples were placed on the surfaces of bovine (diaphyseal) bone surfaces, the size of each samples was 1 cm×1 cm. 50-LB of compressive force was applied to depress the arm and measure the maximum force (N) required to remove the sample from the cow femur bone (see FIGS. 1 and 5).

Example 1

Halloysite nanotubes were loaded with the antibiotic gentamicin and mixed in with PMMA at varying concentrations. Testing showed a sustained release profile of up to 240 hours of the desired substance. Mechanical testing showed a strength and adhesiveness increase that spiked around 7.5% loaded halloysite nanotubes by weight.

Example 2

Halloysite nanotubes were not loaded but mixed with the antibiotic gentamicin or a substance of interest and mixed in with PMMA at varying concentrations.

Example 3

A halloysite loaded nanocomposite used in an orthopedic procedure can be triggered with an ultrasonic device to trigger a secondary burst or release profile of antibiotics to combat infection. A release or burst of other desired substances of interest can be selected from a group consisting of antibiotics, anti-inflammatories, chemotherapeutic agents, bone growth promoting agents, imaging agents and any mixtures thereof to be loaded inside of the halloysite nanotubes.

Example 4

A kit to be used in medical and dental applications comprising halloysite nanotubes, a methylmethacrylate monomer, a polymethylmethacrylate polymer and quantities of beneficial pharmaceutically effective compositions selected from a group consisting of antibiotics, anti-inflammatories, chemotherapeutic agents, bone growth promoting agents, imaging agents and any mixtures thereof to be loaded inside of the halloysite nanotubes or mixed in beside them.

In an alternate embodiment, nanotube clay materials other than halloysite may be used for strengthening. One such material is Imogolite (another aluminosilicate nanotube), generally being up to 1 micron with a maximum diameter of 2 nm. This small diameter reduces the options to load the nanotube with other compounds, but Imogolite could strengthen a bone cement which has been weakened with the admixture of antibiotics.

Numerous modifications will be apparent to those skilled in the art in view of the foregoing description. Accordingly, this description is to be construed as illustrative only and is presented for the purpose of enabling those skilled in the art to make and use what is herein disclosed and to teach the best mode of carrying out same. The exclusive rights to all modifications which come within the scope of this disclosure are reserved.

What is claimed is:

1. An augmented ceramic composite, comprising:
   radiated aluminosilicate nanotubes dispersed in a biocompatible polymer matrix;
   at least one pharmaceutically effective composition; and
   wherein the aluminosilicate nanotubes comprise halloysite nanotubes, the biocompatible polymer matrix comprises polymethylmethacrylate (PMMA), and the halloysite nanotubes are disaggregated and dispersed in the PMMA to form an implantable body selected from a group consisting of a bone cement and a dental composite.

2. The augmented ceramic composite of claim 1, wherein the halloysite nanotubes have a length of about 300 to about 2000 nanometers and a diameter of about 10 to about 300 nanometers.

3. The augmented ceramic composite of claim 2, wherein the nanotubes have the length of about 500 to about 1500 nanometers and the diameter of about 30 to about 100 nanometers.

4. The augmented ceramic composite of claim 1, the implantable body having a maximum force displacement greater than a second body would have had if the second body comprised PMMA with the at least one pharmaceutically effective composition but without halloysite nanotubes.

5. The augmented ceramic composite of claim 2, wherein said halloysite nanotubes are provided at a weight percentage of about 0.005 to about 20.0 percent.

6. The augmented ceramic composite of claim 5, wherein said halloysite nanotubes are provided at a weight percentage of about 2 to about 15 percent.

7. An augmented ceramic composite, comprising:
radiated aluminosilicate nanotubes dispersed in a biocompatible polymer matrix;
wherein the aluminosilicate nanotubes comprise halloysite nanotubes; and
the halloysite nanotubes, the polymer matrix, and at least one pharmaceutically effective composition form an implantable body.

8. The augmented ceramic composite of claim 1, wherein hollow spaces in said halloysite nanotubes comprise the at least one pharmaceutically effective composition selected from a group consisting of antibiotics, anti-inflammatories, bone growth promoting agents, imaging agents, and other chemotherapeutic agents, and any mixtures thereof.

9. The augmented ceramic composite of claim 8, wherein between about 10% to about 40% of the void volume of the nanotubes are filled with the pharmaceutically effective composition.

10. The augmented ceramic composite of claim 1, wherein said halloysite nanotubes are not loaded and the polymethylmethacrylate matrix comprises the at least one pharmaceutically effective composition selected from a group consisting of antibiotics, anti-inflammatories, bone growth promoting agents, imaging agents, and other chemotherapeutic agents, and any mixtures thereof.

11. A method of preparing and/or implanting a biocompatible augmented ceramic composite, comprising: sterilizing halloysite nanotubes with at least radiation; mixing said halloysite nanotubes in a methylmethacrylate monomer; disaggregating said halloysite nanotubes; adding polymethylmethacrylate polymer to the halloysite nanotube-methylmethacrylate monomer mixture; and vacuum mixing.

12. A bone cement or dental composite, comprising:
an implantable body comprising a biocompatible augmented ceramic composite comprising radiated halloysite nanotubes dispersed in a polymer of polymethylmethacrylate dissolved in a reactive monomer of methylmethacrylate.

13. The augmented ceramic composite of claim 1, wherein the halloysite nanotubes comprise sterilized halloysite nanotubes.

14. The method of claim 11, further comprising the step of providing bone growth promoting agents and wherein the augmented ceramic composite comprises bone growth promoting agents.

15. The method of claim 11, further comprising the step of providing a pharmaceutically effective composition selected from a group consisting of antibiotics, anti-inflammatories, bone growth promoting agents, imaging agents, and other chemotherapeutic agents, and any mixtures thereof; and wherein the augmented ceramic composite comprises the pharmaceutically effective composition.

16. The bone cement or dental composite of claim 12, wherein the halloysite nanotubes comprise sterilized halloysite nanotubes.

17. The bone cement or dental composite of claim 12, further comprising a pharmaceutically effective composition selected from a group consisting of antibiotics, anti-inflammatories, bone growth promoting agents, imaging agents, and other chemotherapeutic agents, and any mixtures thereof; and
the implantable body having a maximum force displacement greater than a second body would have had if the second body comprised PMMA with the pharmaceutically effective composition but without halloysite nanotubes.

18. The method of claim 15, further comprising the step of:
implanting the biocompatible augmented ceramic composite; and
wherein the composite has a maximum force displacement greater than a second composite would have had if the second composite comprised PMMA with the pharmaceutically effective composition but without halloysite nanotubes.

19. The augmented ceramic composite of claim 7, wherein the at least one pharmaceutically effective composition is selected from a group consisting of antibiotics, anti-inflammatories, bone growth promoting agents, imaging agents, and other chemotherapeutic agents, and any mixtures thereof.

20. The augmented ceramic composite of claim 7, wherein the implantable body is bone cement.

* * * * *